United States Patent [19]

Horres, Jr.

[11] Patent Number: 4,529,706

[45] Date of Patent: Jul. 16, 1985

[54] METHOD OF STIRRING

[75] Inventor: C. Russell Horres, Jr., Chapel Hill, N.C.

[73] Assignee: Becton Dickinson and Company, Paramus, N.J.

[21] Appl. No.: 476,148

[22] Filed: Mar. 17, 1983

[51] Int. Cl.[3] .......................... G01N 33/48; G01N 1/00

[52] U.S. Cl. .......................... 436/63; 366/165; 436/174

[58] Field of Search .......................... 436/126, 174, 63; 366/165; 356/427

[56] References Cited

U.S. PATENT DOCUMENTS

| | | | |
|---|---|---|---|
| 3,398,935 | 8/1968 | Liuesey et al. | 366/165 X |
| 4,135,818 | 1/1979 | Kent et al. | 356/427 X |
| 4,288,228 | 9/1981 | Oberhardt | 436/178 |

FOREIGN PATENT DOCUMENTS

| | | | |
|---|---|---|---|
| 924969 | 9/1965 | Japan | 366/165 |

OTHER PUBLICATIONS

Hawley, G. G., *The Condensed Chemical Dictionary*, Van Nostrand Reinhold Company Inc., N.Y., 1981, pp. 470–471 and 501.

*Primary Examiner*—Arnold Turk

*Attorney, Agent, or Firm*—Elliot M. Olstein

[57] ABSTRACT

A material is stirred in a container without contact with the container walls by suspending and stirring the material in a vortex generated in a liquid in the container which liquid is immiscible with and has a density greater than the material.

17 Claims, 9 Drawing Figures

FIG-1
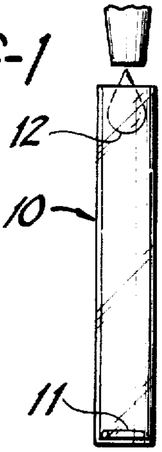
FIG-2
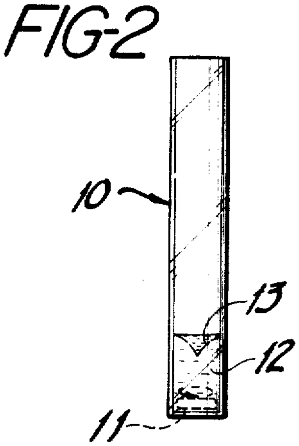
FIG-3
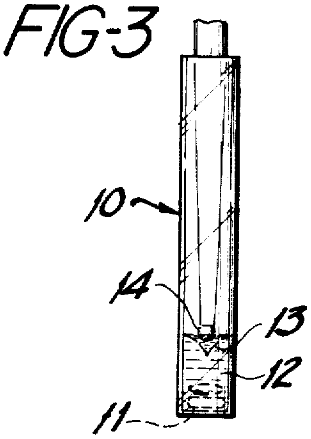
FIG-4
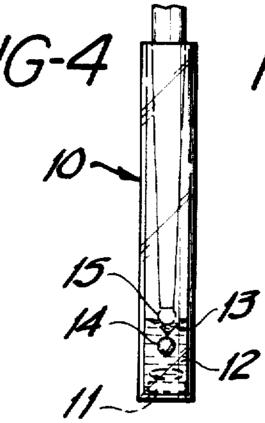
FIG-5
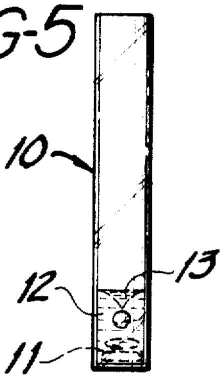
FIG-6
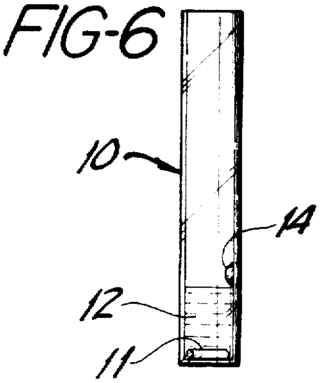
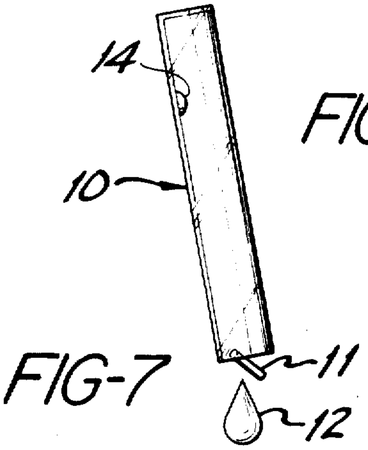
FIG-7
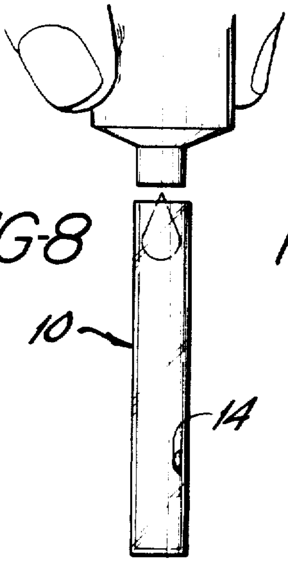
FIG-8
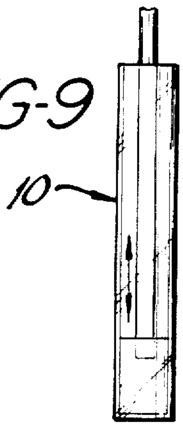
FIG-9

METHOD OF STIRRING

This invention relates to stirring.

In many cases, it is highly desirable to stir a material in a container without the material touching the walls of the container. Thus, for example, in evaluating platelet function by inducing platelet-to-platelet adhesion or aggregation in whole blood or plasma, contact of the platelets with a solid surface, such as a container wall, may result in loss of platelets through adhering of the platelets to the wall. Accordingly, it would be desirable to stir a sample containing such platelets to induce platelet-to-platelet adhesion without the platelets touching the wall.

In accordance with the present invention, there is provided a method of stirring a material or materials in a container without such materials touching the container wall.

More particularly, a fluid is placed in a container and a vortex is generated in such fluid. The material or materials to be stirred are placed and confined in the vortex to prevent the materials from contacting the container walls.

The fluid which is in the container, and in which the vortex is generated, is generally a liquid which is immiscible with the material(s) being stirred, with the fluid having a density greater than such material or materials. In addition, the liquid should be inert with respect to the material or materials to be stirred so as to prevent reaction between the liquid and such materials.

The liquid may be any one of a wide variety of liquids in which a stable vortex can be induced, and which has the properties hereinabove noted as to density and inertness. The liquid selected will be dependent upon the material or materials to be stirred in the vortex; for example, if the material to be stirred is an aqueous liquid, the liquid in which the vortex is to be generated would be a liquid which is immiscible with the aqueous liquid, such as an organic liquid. Conversely, if an organic liquid or liquids are to be stirred, the liquid in which the vortex is to be generated could be an aqueous liquid.

As a representative example of a suitable liquid in which a stable vortex may be generated, and which would be immiscible with an aqueous material to be stirred, there may be mentioned fluorocarbons; e.g., the fluorocarbon sold under the trademark FC-75 by 3M Company.

The stable vortex is preferably generated in the liquid in the container by use of a stirring element in such liquid, such as, for example, a magnetic stirrer. The use of other mechanisms for generating a stable vortex (such as by turning the container) should be apparent to those skilled in the art from the teachings herein.

The stirring rate which is required to produce a stable vortex would be dependent upon the liquid used, and the materials to be stirred therein. The selection of a proper stirring rate for producing the vortex is deemed to be apparent to those skilled in the art from the teachings herein.

The term "stirring" a material(s) in a vortex is used herein in a generic sense, and includes mixing of two materials and/or stirring for the purpose of promoting heat and/or gas transfer in the stirred material; for example, incubation of the material and/or materials in the vortex. The term incubating in the context of this application is used generically to imply the transfer of heat or gaseous matter through the suspending material into or out of the suspended material. An example of this use would be the storage of blood at 37° C. in an oxygenated atmosphere. This is particularly useful in the case of fluorocarbons as the suspending medium because of the high solubility of oxygen in this material. In such a case, oxygen would be dissolved in the immiscible liquid used as a suspending medium (for example, a fluorocarbon), which is maintained at a temperature suitable for maintaining blood at a temperature of 37° C. A blood sample is suspended in the vortex, and both heat and oxygen are transferred to the sample in the vortex from the immiscible fluid.

In accordance with one embodiment, materials are mixed in the vortex, with the process having particular applicability to mixing of small volumes of material (less than 500 microliters), for which conventional mixing procedures would provide a large ratio of surface to volume.

Although the term "mixing" has been used herein, it is to be understood that such term is used in a generic sense, and includes mixing two materials for the purposes of reaction between such materials. Thus, the term "mixing" as used herein generically covers mixing of two reactants, and reaction thereof or combining during the mixing in the vortex.

The procedure of the present invention has particular applicability to a test for evaluating platelet function by inducing platelet-to-platelet adhesion or aggregation. As known in the art, platelet aggregation may be evaluated by changes in light transmission of a platelet rich plasma solution or changes in electrode impedance in a solution of whole blood when a substance known to induce aggregation is added. Both light transmission and electrode impedance methods require citrated blood samples, but the light transmission method requires the sample to be free of red blood cells, which is accomplished by centrifugation under conditions which sediment red blood cells but not platelets. All sample handling is in either plastic or siliconized glass containers to prevent platelet loss by adhesion. The reaction wells of the light transmission method and electrode impedance method are equipped with mechanical stirring devices and there is direct contact between the wells and sample whereby platelet aggregates may adhere to solid surfaces. Instruments are generally heated to evaluate platelet reactivity at 37° C. To conduct an evaluation, samples 200–500 ul in volume are placed in the reaction well, equilibrated and then an aggregating agent is added. By means of a photo optical detector or electrode impedance monitor a temporal recording of light transmission or electrode impedance is obtained. The characteristics of these recordings such as rate change, pattern of change and extent of change provide a semiquantitative evaluation of platelet aggregation. Agents known to induce aggregation include collagen, adenosine diphosphate, ristocetin, epinephrine, 5-hydroxytryptamine, thrombin and others.

In accordance with an aspect of the present invention, platelet-to-platelet aggregation or adhesion is induced in a vortex generated in an immiscible fluid, as hereinabove described. Thus, by proceeding in accordance with the present invention, the platelet-to-platelet adhesion can be induced in a vortex generated in an immiscible fluid to thereby prevent contact between the platelets and the solid surfaces; namely, the container walls, thereby preventing platelet adhesion to solid surfaces.

The present invention is particularly useful for evaluating platelet aggregation in whole blood whereby the added complication of release of endogenous aggregating agents from red blood cells during interaction with solid surfaces is avoided.

The invention will be further described with reference to the accompanying drawings, wherein:

The drawings of FIG. 1 through 9 illustrate a step-by-step procedure for inducing platelet aggregation in accordance with the mixing method of the present invention.

Referring now to the drawings, as shown in FIG. 1, there is provided a container 10 which includes a stirring element 11, such as a magnetic stirrer. A liquid 12 in which a vortex is to be generated, such as for example, a fluorocarbon, in particular FC-75$^R$, is introduced into the container 10.

As shown in FIG. 2, the stirring element mixes the liquid 12 to form a stable vortex 13 therein. The liquid 12 is inert with respect to a blood sample, more dense than the blood sample, and immiscible therewith.

As shown in FIG. 3, a blood sample 14, for example, whole blood or platelet enriched plasma, preferably whole blood, is introduced into the vortex 13 in liquid 12.

As shown in FIG. 4, a material 15 to induce platelet aggregation, such as collagen, is introduced into the vortex 13 of liquid 12 for admixture with the blood sample 14.

As shown in FIG. 5, platelet-to-platelet aggregation is induced, with such inducing being confined within the vortex 13 of liquid 12, whereby the blood sample and collagen are prevented from coming into contact with the walls of vessel 10.

As shown in FIG. 6, after stirring is stopped, the blood sample rises to the surface of the vessel 10 and adheres to the walls thereof. The walls may be siliconized to prevent spreading.

As shown in FIG. 7, with the sample adhering to the walls of vessel 10, the liquid 12 is poured out of container 10, to provide a container free of such liquid, with the blood sample being adhered to the walls thereof.

The sample 14 may be recovered from the vessel after displacement of the suspending fluid by adding isotonic saline or a suitable platelet counting diluent as shown in FIG. 8 and by stirring as shown in FIG. 9. The sample may then be transferred to a counting apparatus.

As should be apparent from the description, it is possible to evaluate platelet function by inducing platelet-to-platelet adhesion, without the platelets coming into contact with the wall of the container during such mixing.

The present invention will be further described with respect to the following examples; however, the scope of the invention is not to be limited thereby:

EXAMPLE

Whole Blood Platelet Aggregation

1. A flat bottomed siliconized glass vessel with a diameter of approximately 6.5 mm is used as the container.
2. Into the vessel, a magnetic stirring bar of the dimensions 1.19 mm diameter and 6.25 mm length is placed and the vessel is located into a thermostated 37° C. block equipped with a magnetic stirrer adjusted to rotate the bar at 1260 revolutions per minute.
3. The vessel is then filled with 0.3 ml of fluorocarbon liquid FC-75$^R$ and allowed to equilibrate for 3 minutes.
4. A 10 ul aliquot of citrated whole blood (3.8 mg citrate/ml) is added to the vortex to the fluorocarbon and allowed to equilibrate for 30 seconds.
5. A 5 ul aliquot of collagen reagent (between 1 and 100 ug/ml) is added to the blood sample and the reaction is timed for five minutes.
6. After five minutes the stirring is stopped and the fluorocarbon is quickly poured off. The blood sample is diluted with approximately 0.5 ml of Clay Adams Unopette fluid and briefly mixed, without shaking.
7. The diluted sample is transferred to a counting reservoir and counted on a whole blood platelet counter.
8. An additional blood sample is stirred without addition of collagen and used as a control for spontaneous aggregation.
9. The degree of aggregation is determined by the differences in the platelet count between the control, non-stirred sample, and the collagen containing sample.
10. Alternatively, the reaction can be performed in platelet rich plasma and counted on a conventional platelet counter.
11. Results may be also obtained by stopping the reaction at different incubation times.
12. The sample may be stabilized for counting at a later time by including 0.25% glutaraldehyde in the diluting fluid.

Numerous modifications and variations of the present invention are possible in light of the above teachings and, therefore, within the scope of the appended claims, the invention may be practiced otherwise than as particularly described.

What is claimed is:

1. A process for stirring at least one material in a container without such material contacting a wall of the container, comprising:

generating a vortex in a suspending liquid in a container;

placing in the vortex at least one material to be stirred, said material being immiscible with said liquid, said material having a density less than said liquid, said liquid being inert with respect to said material; and stirring said at least one material confined in said vortex without said at least one material touching a wall of the container.

2. The process of claim 1 wherein the suspending liquid transfers heat to the at least one material during stirring.

3. The process of claim 1 wherein the suspending liquid has a gas dissolved therein and gas is transferred from the suspending liquid to the at least one material.

4. The process of claim 1 wherein the at least one material is a liquid.

5. The process of claim 1 wherein the suspending liquid is a fluorocarbon.

6. The process of claim 1 wherein the at least one material is a liquid sample in an amount of no greater than 500 ul.

7. The process of claim 1 wherein the at least one material is a blood sample.

8. The process of claim 7 wherein oxygen is dissolved in the suspending liquid, and oxygen is transferred from the suspending liquid to the blood sample during said stirring.

9. The process of claim 7 wherein a platelet aggregating agent is admixed with the blood sample in the vortex to induce platelet aggregation.

10. The process of claim 9 wherein after platelet aggregation the blood sample is stabilized with glutaraldehyde.

11. A process for aggregating platelets in a blood sample, comprising:

generating a vortex in a suspending liquid in a container, said suspending liquid being immiscible with blood, having a density greater than blood and being inert with respect to the blood;

placing a blood sample and an aggregating agent in the vortex;

mixing the aggregating agent and blood sample in the vortex to induce platelet aggregation in the blood sample in the vortex without the blood sample touching a wall of the container; and recovering the blood sample containing aggregated platelets.

12. The process of claim 11 wherein the suspending liquid is a fluorocarbon.

13. The process of claim 11 wherein the blood sample is whole blood.

14. The process of claim 11 wherein the blood sample is no greater than 500 ul.

15. The process of claim 11 wherein the blood sample is platelet rich plasma.

16. The process of claim 11 wherein after recovery of the sample unaggregated platelets are counted.

17. The process of claim 16 wherein the recovered sample is stabilized with glutaraldehyde.

* * * * *